(12) United States Patent
Baxi et al.

(10) Patent No.: US 9,345,415 B2
(45) Date of Patent: May 24, 2016

(54) METHOD AND APPARATUS FOR MEASURING MULTIPLE ECG LEADS USING A DEVICE WITH EMBEDDED LEADS

(71) Applicants: Amit S. Baxi, Bangalore (IN);
Raghavendra Rao R, Bangalore (IN)

(72) Inventors: Amit S. Baxi, Bangalore (IN);
Raghavendra Rao R, Bangalore (IN)

(73) Assignee: INTEL CORPORATION, Santa Clara, CA (US)

( * ) Notice: Subject to any disclaimer, the term of this patent is extended or adjusted under 35 U.S.C. 154(b) by 422 days.

(21) Appl. No.: 13/726,854

(22) Filed: Dec. 26, 2012

(65) Prior Publication Data

US 2013/0172723 A1  Jul. 4, 2013

(30) Foreign Application Priority Data

Dec. 30, 2011 (IN) .......................... 3879/DEL/2011

(51) Int. Cl.
| | | |
|---|---|---|
| *A61B 5/0408* | (2006.01) | |
| *A61B 5/0432* | (2006.01) | |
| *A61B 5/00* | (2006.01) | |
| *A61B 5/0404* | (2006.01) | |

(52) U.S. Cl.
CPC ........... *A61B 5/04085* (2013.01); *A61B 5/0404* (2013.01); *A61B 5/0432* (2013.01); *A61B 5/04325* (2013.01); *A61B 5/6825* (2013.01); *A61B 5/6823* (2013.01); *A61B 2560/0468* (2013.01)

(58) Field of Classification Search
CPC ...................... A61B 5/0404; A61B 2560/0468
USPC .......................................... 600/393, 508, 509
See application file for complete search history.

(56) References Cited

U.S. PATENT DOCUMENTS

| | | | | |
|---|---|---|---|---|
| 4,535,783 A * | 8/1985 | Marangoni | ................... | 600/524 |
| 4,596,256 A * | 6/1986 | Ascher et al. | ................. | 600/523 |
| 5,623,926 A * | 4/1997 | Weiss | ............................ | 600/509 |
| 8,244,336 B2 * | 8/2012 | Wang et al. | ................... | 600/509 |
| 2003/0097078 A1 * | 5/2003 | Maeda | .......................... | 600/509 |
| 2004/0260190 A1 * | 12/2004 | Tanabe et al. | ................. | 600/509 |
| 2005/0004487 A1 * | 1/2005 | Ishida et al. | ................. | 600/523 |
| 2006/0047210 A1 * | 3/2006 | Moroki et al. | ................ | 600/509 |
| 2006/0217620 A1 * | 9/2006 | Bojovic et al. | ................ | 600/509 |
| 2007/0149887 A1 * | 6/2007 | Hwang et al. | ................. | 600/509 |

FOREIGN PATENT DOCUMENTS

WO   WO 2011/040877 A1 *   4/2011

* cited by examiner

*Primary Examiner* — Carl H Layno
*Assistant Examiner* — Jennifer Ghand
(74) *Attorney, Agent, or Firm* — Buckley, Maschoff & Talwalkar LLC

(57) ABSTRACT

An apparatus and a method, the apparatus including a housing, an electrocardiogram (ECG) measuring circuit contained in the housing, and three electrodes embedded in the housing, electrically connected to the ECG measuring circuit, and in spaced apart configuration from each other.

12 Claims, 5 Drawing Sheets

700

MEASURE, USING A PEM HAVING THREE EMBEDDED
ELECTRODES, AN ECG LEAD 1
705

MEASURE, USING THE PEM, ECG LEADS 2 AND LEAD 3
710

MEASURE, USING THE PEM, MODIFIED CHEST LEADS
(e.g., MCL-1 THROUGH MCL-6)
715

METHOD AND APPARATUS FOR MEASURING MULTIPLE ECG LEADS USING A DEVICE WITH EMBEDDED LEADS

BACKGROUND

The recording of electrical activity of the heart is known as an Electrocardiogram (ECG). An ECG measures the differential electrical signal between a pair of electrodes of an ECG device. A pair of electrodes of the ECG device is referred to as an ECG lead. Conventional methods of recording an ECG involve placing 10 adhesive electrodes on the chest, torso, and possibly the extremities of a patient to record different ECG leads derived from differential potentials between different combinations of the electrodes.

In a clinical environment, ECG machines to record multiple ECG leads have multiple ECG electrodes connected to an ECG device via electrical cables and clips. The multiple ECG leads enable a physician to "view" the heart from different directions. The different "views" of the heart may assist the physician in diagnosing a heart condition of the patient. This type of ECG setup however requires numerous accessories to connect the patient to the ECG device, such as disposable electrodes and ECG cables. Additionally, such a procedure requires expertise to setup and administer the ECG and may not be comfortable for the patient.

In some recent developments, a variety of Personal ECG Monitors (PEM) have been produced. In part, the PEMs seek to address the usability problem of traditional ECGs by using two metal electrodes embedded on the ECG device itself. The PEM operates to record an ECG by having the patient either hold the device in their hand or against their chest so that the metal electrodes of the device touch the patient's body. In this manner the PEM is able to effectuate a single ECG lead. However, PEMs are limited in their diagnostic capability since they typically do not measure more than one ECG lead. In many aspects, a single ECG lead is insufficient to detect some serious heart conditions (e.g., ischemia and infarction).

BRIEF DESCRIPTION OF THE DRAWINGS

Aspects of the present disclosure herein are illustrated by way of examples and not by way of limitation in the accompanying figures. For purposes related to simplicity and clarity of illustration rather than limitation, aspects illustrated in the figures are not necessarily drawn to scale. Further, where considered appropriate, reference labels have been repeated among the figures to indicate corresponding or analogous elements.

DETAILED DESCRIPTION

The disclosure herein provides numerous specific details such regarding a system for implementing various processes and operations. However, it will be appreciated by one skilled in the art(s) related hereto that embodiments of the present disclosure may be practiced without such specific details. Those of ordinary skill in the art will be able to implement appropriate functionality without undue experimentation given the included descriptions herein.

References in the specification to "one embodiment", "some embodiments", "an embodiment", "an example embodiment", "an instance", "some instances" indicate that the embodiment described may include a particular feature, structure, or characteristic, but that every embodiment may not necessarily include the particular feature, structure, or characteristic. Moreover, such phrases are not necessarily referring to the same embodiment. Further, when a particular feature, structure, or characteristic is described in connection with an embodiment, it is submitted that it is within the knowledge of one skilled in the art to affect such feature, structure, or characteristic in connection with other embodiments whether or not explicitly described.

Some embodiments herein may be implemented in hardware, firmware, software, or any combinations thereof. Embodiments may also be implemented as executable instructions stored on a machine-readable medium that may be read and executed by one or more processors. A machine-readable storage medium may include any tangible non-transitory mechanism for storing information in a form readable by a machine (e.g., a computing device). In some aspects, a machine-readable storage medium may include read only memory (ROM); random access memory (RAM); magnetic disk storage media; optical storage media; flash memory devices; and electrical and optical forms of signals. While firmware, software, routines, and instructions may be described herein as performing certain actions, it should be appreciated that such descriptions are merely for convenience and that such actions are in fact result from computing devices, processors, controllers, and other devices executing the firmware, software, routines, and instructions.

Figure 1:
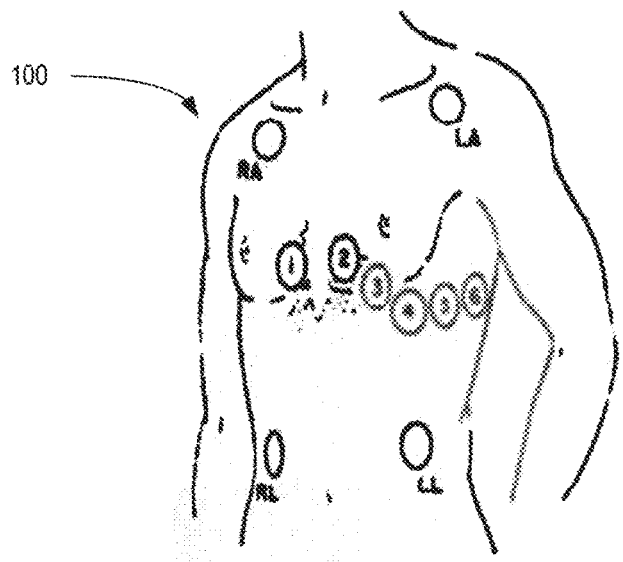
FIG. 1 is an illustrative depiction of the conventional electrode positions for an ECG.

FIG. 1 is an illustrative depiction of the conventional electrode positions 100 for an ECG measurement. The depicted electrode positions include a Right Arm electrode position (RA), a Left Arm electrode position (LA), a Left Leg electrode position (LL), a Right Leg electrode position (RL), and six chest electrode positions V1 to V6. Lead-1 (L1) is a potential difference between the electrode on Left Arm (LA) and the Right Arm (RA) electrode and is represented as Lead-1=L1=LA-RA. Similarly, other ECG leads are computed as Lead-2=L2=LL-RA and Lead-3=L3=LL-LA.

In addition to the leads discussed above, there are also six modified chest leads (MCL) that measure differential signals between each of the conventional chest electrode positions (e.g., positions 1 through 6 in FIG. 1) and the left Arm (LA), respectively. Accordingly, Modified Chest Lead-1=MCL1=Chest electrode V1-LA; Modified Chest Lead-2=MCL2=Chest electrode V2-LA. In a similar manner, modified Chest Leads 3-6 can be measured.

It is noted that scientific literature documents and accepts that the modified chest leads appear similar in waveform shape and morphology to conventional chest leads. Thus, the six modified chest leads (i.e., MCL1-MCL6) may be used in lieu of conventional chest leads (V1-V6).

Figure 2:
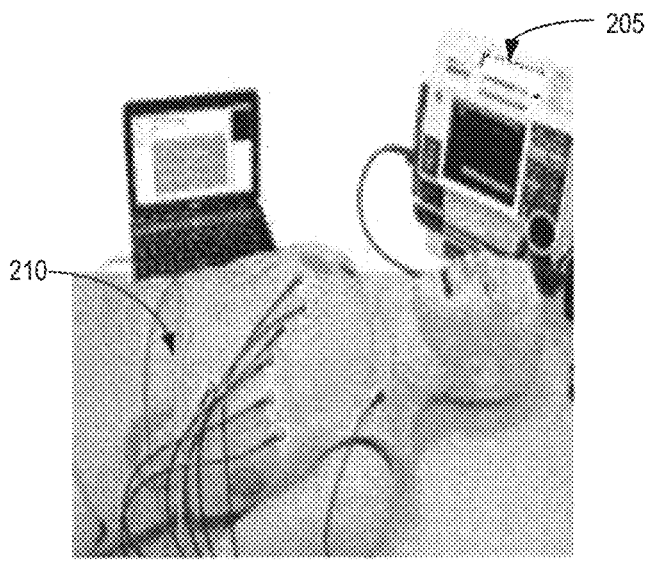
FIG. 2 is an illustrative depiction of a conventional ECG setup.

FIG. 2 is a depiction of a conventional ECG setup, including an ECG device 205 and ten electrodes 210 connected to a patient. As shown, this configuration of equipment and patient is not readily suitable of quick and/or efficient measurement of an ECG.

Figure 3:
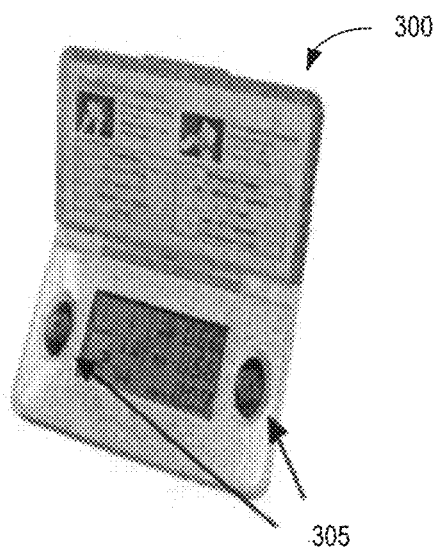
FIG. 3 is an illustrative depiction of a conventional personal ECG monitor.

FIG. 3 shows a conventional PEM 300 including two electrodes 305 in the ECG device. To record an ECG, a patient either holds the device in his hand(s) or touches it to their chest so that the metal electrodes touch their body, thus completing a single ECG lead. While offering some measure of portability the PEM 300 does not measure more than one ECG lead. In some respects it is important to measure at least three orthogonal ECG leads, such as for example, Lead-1 (L1), Lead-2 (L2) and chest lead. PEMs having two electrode leads cannot measure, for example, chest leads V1-V6 that contain important diagnostic information regarding a measured heart using the two electrodes of the conventional PEM.

Figure 4:
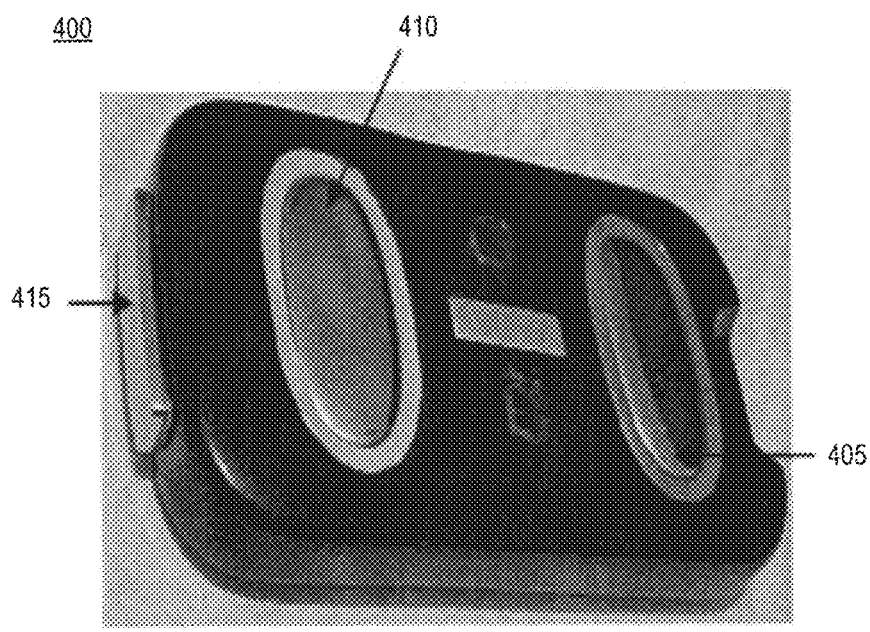
FIG. 4 is an illustrative depiction of a personal ECG monitor, in accordance with an embodiment herein.

According to some embodiments, FIG. 4 is an illustrative rendering of an apparatus for measuring multiple ECG leads by electrodes embedded on or within a PEM 400. PEM 400 includes three embedded electrodes. The three electrode PEM may be combined with a multi-ECG lead measurement method (described in detail below) to provide improved diagnostic capabilities and greater efficiency and usability. PEM 400 includes a first electrode 405 (E1), a second electrode 410 (E2), and a third electrode 415 (E3). PEM 400 may be used to measure nine (9) different ECG leads without the use of adhesive electrodes and cables.

As shown PEM 400 includes the three metal electrodes (E1, E2, and E3) mounted on or in surfaces of a portable device, thus enabling the measurement of different ECG leads. In the embodiment of FIG. 4, two of the electrodes (e.g., 405, E1 and 410, E2) are mounted on or in a first surface of the device and one of the electrodes (e,g, 415, E3) is mounted on another surface the device. The three electrodes are spaced apart from each other such that each electrode may be touched or placed in contact with a hand, finger or other body part of a "patient" without interference with any of the other electrodes.

It should be understood that the configuration of the three electrodes may be modified from the exact example of FIG. 4 and such modifications are considered within the scope of the present disclosure.

Figure 5:
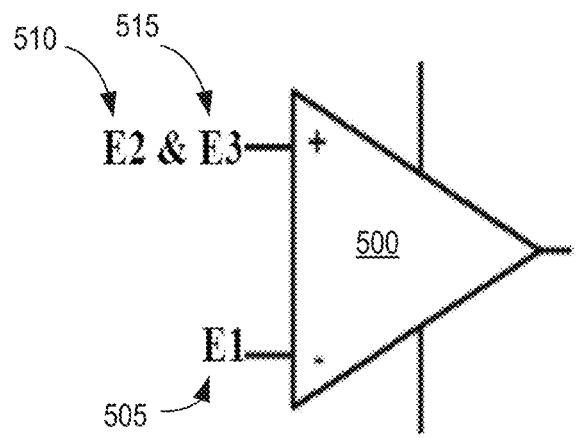
FIG. 5 an illustrative schematic diagram for a personal ECG monitor, in accordance with one embodiment herein.

In some embodiments, the apparatus of the present disclosure may contain an ECG amplifier circuit that is electrically connected to the electrodes thereof. FIG. 5 is a schematic diagram of an amplifier 500 electrically connected to electrodes 505 (E1), 510 (E2), and 515 (E3). As shown, two of the electrodes (e.g., 510 and 515) may be connected to one of the inputs of the amplifier 500 and the remaining electrode (e.g., 505) may be connected to the other input. FIG. 5 shows the electrical connection of these electrodes to an ECG amplifier circuit internal to the instrument. Of the three electrodes, 505 (E1) is shown connected to the negative input of the internal ECG amplifier circuit 500 and the other two electrodes 510 (E2) and 515 (E3) are electrically shorted and connected to the positive input of ECG amplifier 500. In some embodiments, the connections of the electrodes to the amplifier or other circuitry may differ from the example of FIG. 5.

The electrode placement and electrical connections of a PEM disclosed herein provides improved measurement accuracy as compared to conventional PEMs since the PEM herein enables measurement of nine different ECG leads—Lead1 (L1), Lead2 (L2), Lead3 (L3) and the six Modified Chest Leads MCL1 through MCL6.

Figure 6A:
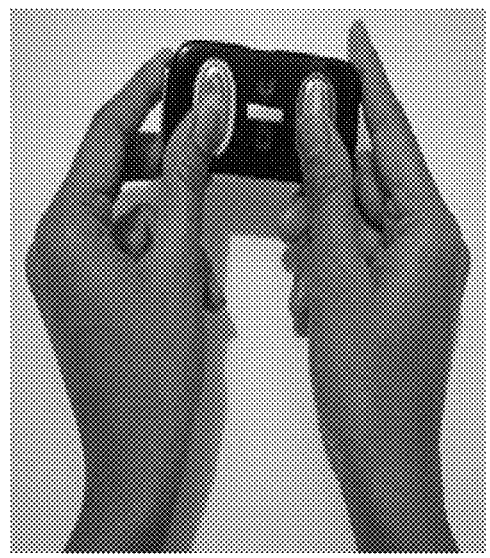
FIGS. 6A-6C illustrate configurations for measuring ECG leads, in accordance with some embodiments herein.
Figure 6B:
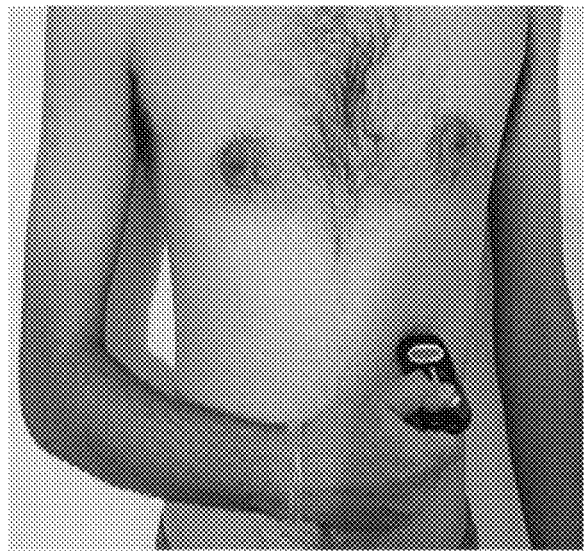
Figure 6C:
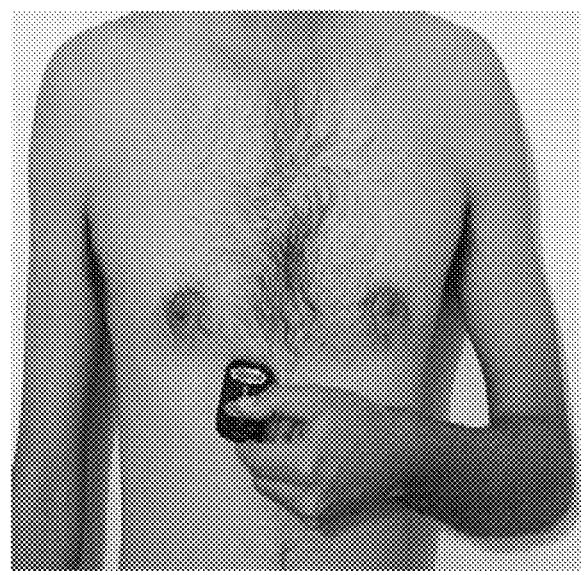

FIGS. 6A-6C are depictions illustrating different manners of holding a PEM conforming to the present disclosure to measure 9 different ECG leads. The measurement of the nine different leads will be presented in reference to FIGS. 6A-6C.

Referring to FIG. 6A, Lead 1 may be measured by having a user hold the device with a thumb of each hand on one of the electrodes E1 and E2. As shown, the left thumb touches electrode E2 and right thumb touches electrode E1.

Measuring Lead 2, the equivalent of the conventional LL-RA lead, may be accomplished by having a user holding the device as shown in FIG. 6B. That is, electrode E1 is held with the right thumb and the side electrode E3 is placed in contact with the user at LL location on the user's torso. In a similar manner, the measurement of Lead 3 may be made by holding electrode E1 with the left thumb and by placing electrode E3 in contact with the user at the LL location.

The PEM disclosed herein as having three electrodes may be used to effectuate the measuring of chest leads MCL1 through MCL6: The PEM herein can measure modified chest leads MCL1 through MCL6. For example, FIG. 6C shows a measurement of MCL1, where the electrode E1 is held with the user's left thumb and the side electrode E3 is placed at the V1 location on the chest of the user. Similarly, other modified chest leads (MCL2 through MCL6) may also be measured by holding E1 with the user's left thumb and touching electrode E3 to the various chest electrode positions (i.e., electrode positions 2-6).

Figure 7:
FIG. 7 is a flow diagram, in accordance with some embodiments herein.
Figure 7:

FIG. 7 is a flow diagram of a process 700 for measuring the different ECG leads with a device including the characteristics disclosed herein, including the three embedded electrodes. At operation 705, a Lead 1 ECG measurement is taken by having a user hold the device with a thumb from each hand on each of the electrodes E1 and E2 (demonstrated in FIG. 6A).

Operation 710 includes measuring Lead 2 and Lead 3. In some embodiments, these ECG measurements may be grouped together since E3 is held at the LL location of the user for both measurements, wherein the E1 contact point varies. In particular, electrode E1 is held with the right thumb and the side electrode E3 is placed in contact with the user at LL location on the user's trunk for measuring Lead 2. In a like manner, the measurement of Lead 3 may be made by holding electrode E1 with the left thumb and by placing electrode E3 in contact with the user at the LL location (reference FIG. 6B).

Operation 715 includes measuring Modified Chest Leads MCL-1 through MCL-6 (i.e., six (6) Leads). Such measurements are demonstrated in FIG. 6C. The electrode E1 is held in contact with the user's left thumb and the side electrode E3 is placed at the appropriate V1 location on the chest of the user to obtain the corresponding MCL Lead.

In some embodiments, a PEM in some aspects herein may include a user interface. The user interface may include a display for communicating graphics and/or text-based information to a user. In some embodiments, the display may include a touch screen. In some embodiments, the PEM device may include one or more user input mechanisms (e.g., a key pad, microphone, numeric keys, etc.), and include one or more components for communicating with another entity, whether a person or a machine. In some aspects, an interface to communicate data or information from the PEM to a user or machine may include a wired or wireless communication link, where the communication protocol is not hereby limited. The aspects of the methods and devices herein may be included or integrated into devices having other functions and capabilities, other than that of the PEM herein. For example, an embodiment of a mobile phone or computing tablet may include the functions and capabilities of the PEM disclosed herein. In some embodiments, the PEM herein may include a memory for storing measurements obtained using the PEM.

Embodiments have been described herein solely for the purpose of illustration. Persons skilled in the art will recognize from this description that embodiments are not limited to those described, but may be practiced with modifications and alterations limited only by the spirit and scope of the appended claims.

What is claimed is:

1. An apparatus comprising:
   a housing;
   an electrocardiogram (ECG) measuring circuit contained in the housing;
   three electrodes embedded in the housing, electrically connected to the ECG measuring circuit, and in spaced apart configuration from each other, wherein two of the three electrodes are arranged on a single surface of the housing and the third electrode is on another surface of the housing; and
   an ECG amplifier comprising a first input and a second input wherein a first of the three electrodes and a second of the three electrodes are connected to the first input and a third of the three electrodes is connected to the second input, wherein the third of the three electrodes is connected to a negative input of the ECG amplifier and the first and second electrodes of the three electrodes are electrically shorted and connected to a positive input of the ECG amplifier.

2. The apparatus of claim 1, wherein the three electrodes are electrically conductive.

3. The apparatus of claim 1, where the ECG measuring circuit, in cooperation with the three electrodes, measures a plurality of ECG Leads.

4. The apparatus of claim 3, wherein the apparatus measures nine ECG Leads.

5. The apparatus of claim 1, further including a memory to store a measurement obtained by the apparatus.

6. A method comprising,
   obtaining a first ECG Lead measurement by measuring a differential electrical signal using two of three electrodes of a device having three electrodes embedded in a housing, the electrodes electrically connected to an ECG measuring circuit in the housing, in spaced apart configuration from each other, and held in the hands of a user wherein the housing comprises an ECG amplifier that includes a first input and a second input and wherein a first of the three electrodes and a second of the three electrodes are connected to the first input and a third of the three electrodes is connected to the second input, wherein the third of the three electrodes is connected to a negative input of the ECG amplifier and the first and second electrodes of the three electrodes are electrically shorted and connected to a positive input of the ECG amplifier;
   measuring a plurality of ECG Lead measurements by measuring a differential electrical signal using two of the three electrodes, one of the electrodes placed in a hand of the user and one of the electrodes placed in contact with a torso portion of the user, wherein two of the three electrodes are arranged on a single surface of the housing and the third electrode is on another surface of the housing.

7. The method of claim 6, further comprising measuring a plurality of ECG Lead measurements by measuring a differential electrical signal using two of the three electrodes, one of the electrodes placed in a hand of the user and one of the electrodes placed in contact with a plurality of contact points on a chest portion of the user.

8. The method of claim 6, wherein the three electrodes are embedded in a body of the device.

9. The method of claim 6, wherein the ECG measuring circuit, in cooperation with the three electrodes, measures a plurality of ECG Leads.

10. The method of claim 9, wherein the device measures nine ECG Leads.

11. The method of claim 6, further comprising storing a measurement obtained by the device in a memory of the device.

12. The method of claim 6, further comprising presenting the plurality of ECG Lead measurements by the device.

* * * * *